US011061033B2

(12) United States Patent
Acharya et al.

(10) Patent No.: US 11,061,033 B2
(45) Date of Patent: Jul. 13, 2021

(54) ASSAY FOR DETECTION OF BLADDER OR PROSTATE CANCER

(71) Applicant: University of Pittsburgh—Of the Commonwealth System of Higher Education, Pittsburgh, PA (US)

(72) Inventors: Abhinav Acharya, Pittsburgh, PA (US); Steven R. Little, Pittsburgh, PA (US); Tatum V. Tarin, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 152 days.

(21) Appl. No.: 16/091,495

(22) PCT Filed: Apr. 5, 2017

(86) PCT No.: PCT/US2017/026172
§ 371 (c)(1),
(2) Date: Oct. 4, 2018

(87) PCT Pub. No.: WO2017/176899
PCT Pub. Date: Oct. 12, 2017

(65) Prior Publication Data
US 2019/0120843 A1    Apr. 25, 2019

Related U.S. Application Data

(60) Provisional application No. 62/318,659, filed on Apr. 5, 2016.

(51) Int. Cl.
*G01N 33/574* (2006.01)
*C12Q 1/37* (2006.01)
*G01N 33/50* (2006.01)

(52) U.S. Cl.
CPC ......... *G01N 33/57407* (2013.01); *C12Q 1/37* (2013.01); *G01N 33/50* (2013.01); *G01N 33/57434* (2013.01); *G01N 2333/96486* (2013.01)

(58) Field of Classification Search
None
See application file for complete search history.

(56) References Cited

U.S. PATENT DOCUMENTS

| | | | | |
|---|---|---|---|---|
| 2003/0206957 A1* | 11/2003 | Scherr | ............... | A61K 2300/00 424/488 |
| 2007/0205157 A1 | 9/2007 | Jones et al. | | |
| 2012/0197415 A1* | 8/2012 | Montanari | ............... | A61L 27/34 623/23.74 |
| 2014/0260468 A1 | 9/2014 | Bezbaruah et al. | | |
| 2015/0342893 A1* | 12/2015 | Coulter | ............... | A61K 31/635 424/490 |

FOREIGN PATENT DOCUMENTS

DE    102008057186 A1 *  5/2010  ............. B01J 13/06
WO    WO 1991/011206      8/1991

OTHER PUBLICATIONS

Definition of "gelatin" downloaded from https://www.dictionary.com/browse/gelatin on Aug. 11, 2020 (Year: 2020).*
Machince translation of DE102008057186 (A1) published May 2010, from Espacenet on Aug. 15, 2020. (Year: 2010).*
Gutierrez Banos et al., "NMP 22, BTA stat test and cytology in the diagnosis of bladder cancer: a comparative study," *Urologia Internationalis*, 66(4): 185-190, May 2001.
International Search Report and Written Opinion issued for International Application No. PCT/US2017/026172 dated Jun. 19, 2017.
Xing et al., "Increasing mechanical strength of gelatin hydrogels by divalent metal ion removal," *Scientific Reports*, vol. 4, 10 pages, Apr. 16, 2014.
Yang et al., "Fabrication of porous gelatin microfibers using an aqueous wet spinning process," *Artificial Cells, Blood Substitutes, and Biotechnology*, 37(4): 173-176, Aug. 13, 2009.

* cited by examiner

*Primary Examiner* — Susan M Hanley
(74) *Attorney, Agent, or Firm* — Klarquist Sparkman, LLP

(57) ABSTRACT

A Fe(II)- and $Ca^{+2}$-chelated alginate/gelatin conjugate.

33 Claims, 12 Drawing Sheets

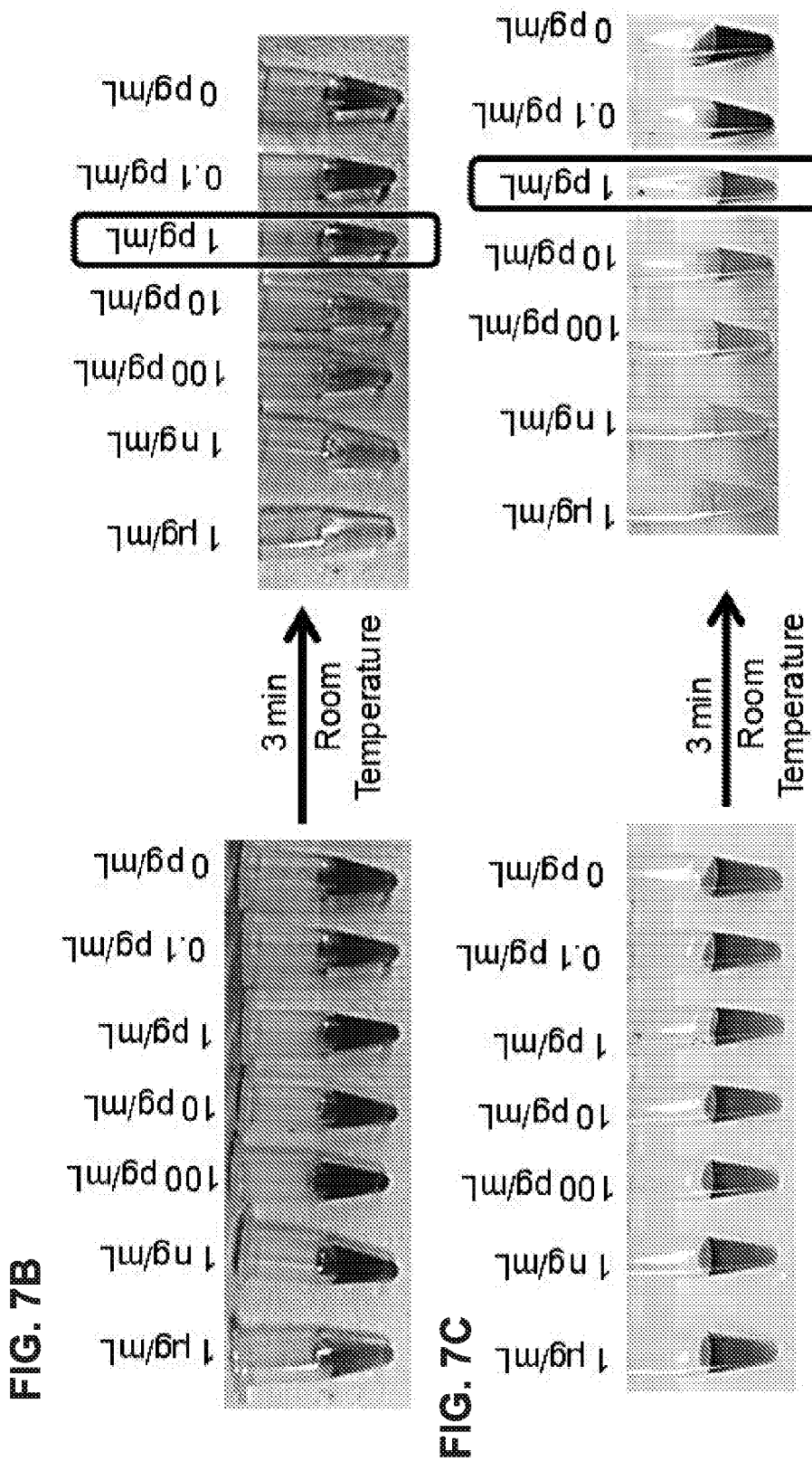

ASSAY FOR DETECTION OF BLADDER OR PROSTATE CANCER

This application is the U.S. National Stage of International Application No. PCT/US2017026172, filed Apr. 5, 2017, which was published in English under PCT Article 21(2), which in turn claims the benefit of U.S. Provisional Appl. No. 62/318,659, filed Apr. 5, 2016, which is incorporated herein by reference.

BACKGROUND

Currently bladder and prostate cancers are the most expensive malignancy because of the regular use of cystoscopy for the follow-up of these patients. In order to decrease the cost from the use of cystoscopy, several urine markers have been developed over the years for regular follow-up. Clinically available tests include NMP-22, urine cytology, FISH, BTA-STAT among others. All these tests are send-off lab tests and are not available for in-clinic use and therefore there is a need for development of technologies that can be used in-clinic in order to decrease the costs. Moreover, these techniques need to have similar sensitivity to existing tests to be able to reliably monitor bladder cancer progression.

Such techniques need to detect biomarkers of bladder and prostate cancers. Several biomarkers for these cancers have been studied. Among them up-regulation of MMP2 and MMP9 (72 kDa and 92 kDa type IV collagenases or gelatinase A and gelatinase B, respectively) has been shown to be involved in cancer metastasis and therefore, is an attractive target to study bladder cancer progression. Moreover, clinical detection of these enzymes in biological fluids can differentiate between aggressive and non-aggressive disease states and be used to monitor disease progression. These MMPs are associated with malignant phenotype of cancer cells because of their ability to degrade type IV collagen, which is a major component of the basement membrane. Moreover, MMP2/9 have been shown to have a strong correlation to unfavorable prognostic factors of urothelial bladder cancer and tumor recurrence and therefore may be useful in the follow up of the patients.

Quantitative detection of MMP2/9 is currently performed using enzyme linked immunosorbent assays (ELISAs—detection limit of $10^{-12}$ M), whereas detection of the active form of enzyme is typically performed using zymography, (detection limit of $30 \times 10^{-15}$ moles). Although, ELISA is quantitative highly sensitive, it cannot determine the active form of the enzymes. On the other hand, zymography can detect the active form of the enzyme, but they are not very sensitive. Both the techniques require sophisticated instruments and trained personnel, and therefore are difficult to implement in clinics. Moreover, it is important to differentiate between benign bladder/prostate disease and cancer, which has been strongly linked to the active form of MMPs in the urine.

SUMMARY

Disclosed herein is a Fe(II)- and $Ca^{+2}$-chelated alginate/gelatin conjugate, which may take the form of particles.

Also disclosed herein is a composition that includes the conjugate. In particular, the composition is a bioassay that includes a plurality of conjugate particles. In certain embodiments, the particles may agglomerate.

Further disclosed herein is a kit comprising:
a composition comprising the conjugate; and
a composition comprising a Fenton reagent and at least one chromogenic substrate. In certain embodiments the conjugate composition and the Fenton reagent composition are provided in separate containers.

Also disclosed herein is method for detecting the presence of cancer in a subject, comprising:
contacting a biological sample from the subject with the conjugate to form a sample/conjugate composition; and
contacting the sample/conjugate composition with a composition that comprises a Fenton reagent at least one chromogenic substrate resulting in an assay composition;
wherein detection of a color change in the assay composition indicates the presence of a matrix metalloproteinase in the biological sample. The presence of a matrix metalloproteinase in the biological sample may be an indicator of the presence of cancer.

Additionally disclosed herein is a method comprising:
contacting a biological sample from a subject with a gelatin-crosslinked aggregate of particles comprising a Fe(II)- and $Ca^{+2}$-chelated alginate or with a Fe(II)-chelated alginate;
generating individual particles via gelatinase-mediated cleavage of the gelatin crosslinks between the particles, wherein the gelatinase is present in the biological sample; and
contacting the individual particles with an acid, $H_2O_2$, and at least one chromogenic substrate.

Further disclosed herein is a composition comprising a gelatin-crosslinked aggregate of particles comprising a Fe(II)- and $Ca^{+2}$-chelated alginate.

Also disclosed herein is a method comprising:
contacting an (i) alginic acid or alginate with (ii) a Fe(II) ion source and, optionally, (iii) a $Ca^{+2}$ ion source resulting in particle comprising Fe(II)-chelated alginate or Fe(II)- and $Ca^{+2}$-chelated alginate;
contacting the particles with an activating agent resulting in activated particles; and
contacting the activated particles with a gelatinase-specific gelatin-type substrate resulting in a gelatin-crosslinked aggregate of particles.

The foregoing will become more apparent from the following detailed description, which proceeds with reference to the accompanying figures.

Step 6. The previously "hidden" Fe (II) catalyst is activated by adding acid to remove the alginic acid chelate, and the assay very effectively generates visually observable color output proportional to the amount of active MMPs 2/9. Steps 4-6 are utilized to identify bladder cancer by detecting collagenase in patient's urine.

Figure 2C:
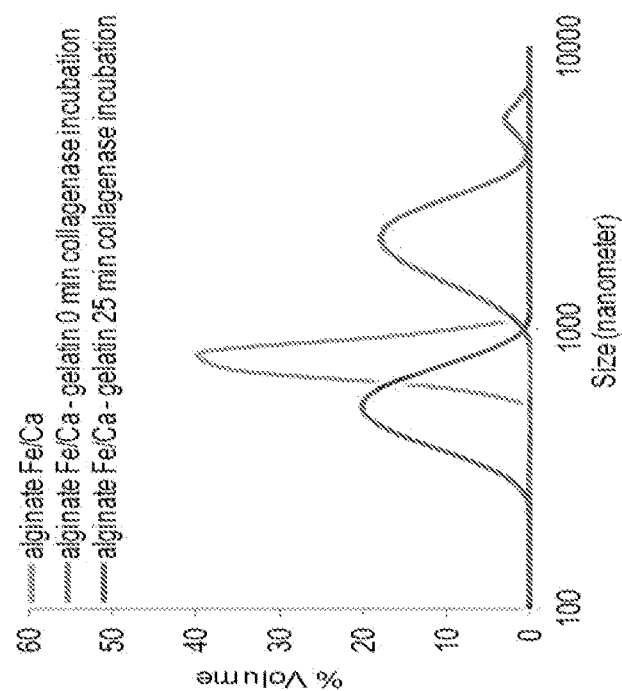
Figure 2B:
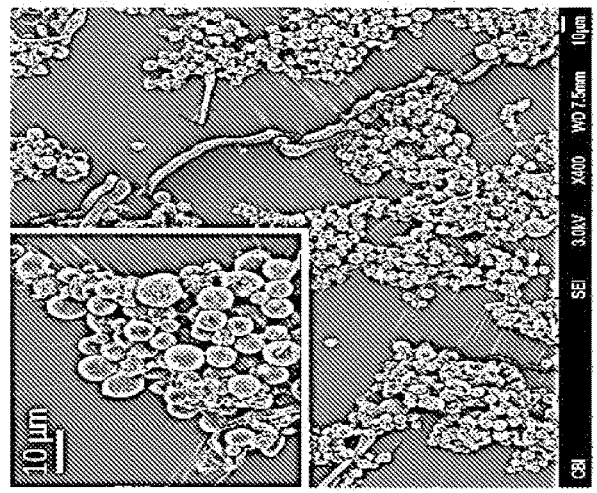
Figure 2A:
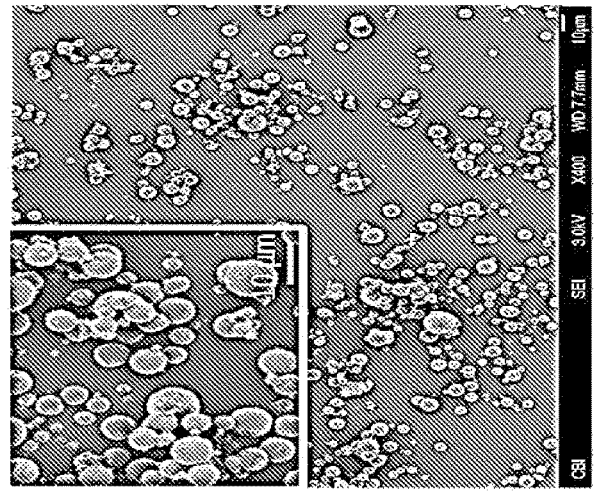

FIGS. 2A-2C show the characterization of Ammps and size change in the presence of collagenase type IV. (FIG. 2A) Alginate (Fe/Ca) particles that were generated via inverse emulsion of alginic acid and chelation of equimolar levels of ferrous chloride and calcium chloride were imaged using SEM. (FIG. 2B) Conjugation of alginate (Fe/Ca) particles with gelatin type A causes aggregation of particles as observed by SEM. (FIG. 2C). The average size of alginate (Fe/Ca) particles, alginate (Fe/Ca)—gelatin conjugated particles and alginate (Fe/Ca)—gelatin conjugated particles in the presence of collagenase was obtained using dynamic light scattering.

Figure 3A:
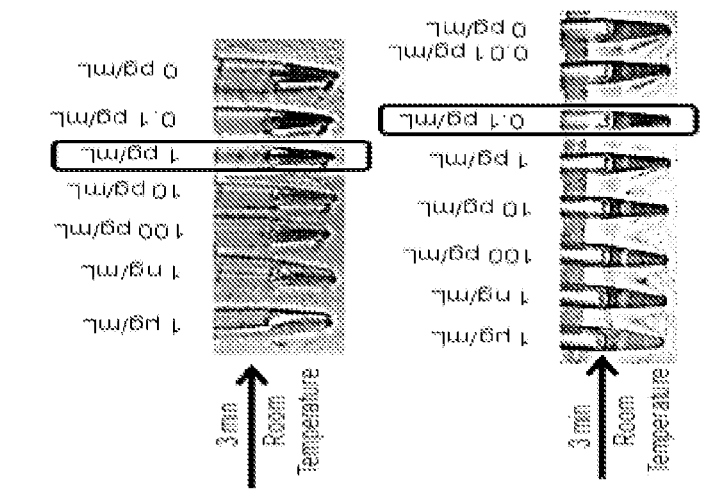
Figure 3B:
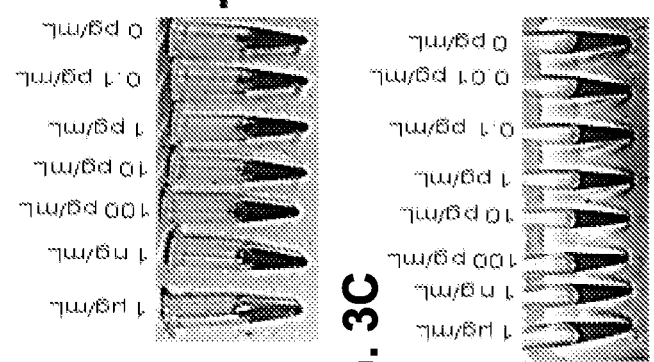
Figure 3C:
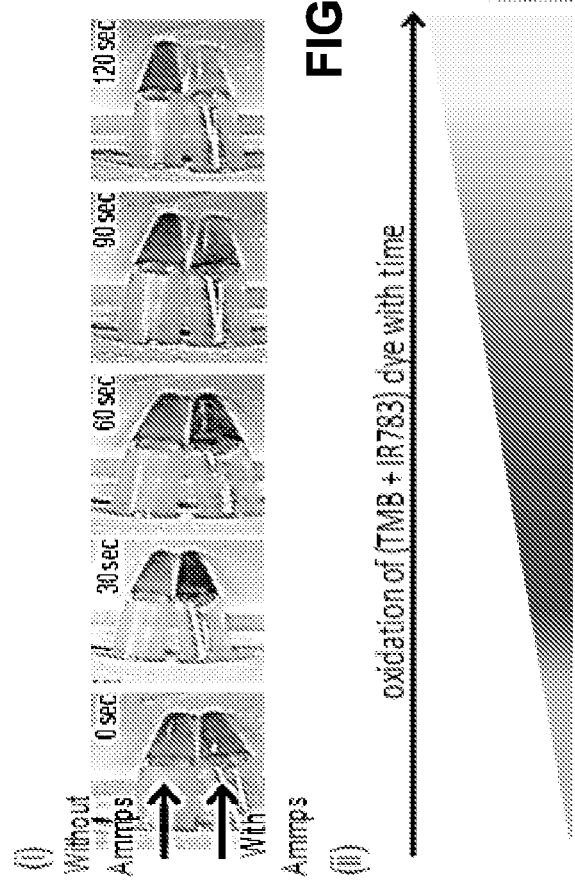

FIGS. 3A-3C: Ammps have a limit of detection of 1 µg/mL in water and urine spiked with collagenase type N. (FIG. 3A) Oxidation of TMB and IR783 dyes (i) in the presence or absence of alginate (Fe/Ca) particles (representative of n=3). (ii) Color key for increasing oxidation of TMB and IR783 in the presence of Ammps with time is shown. (FIG. 3B) Water was spiked with collagenase type N ranging from 1 mg/mL to 0.1 µg/mL and Ammps was performed to detect the limit of detection in water (representative of n=3). (FIG. 3C) Non-diseased urine was spiked with collagenase type N ranging from 1 µg/mL to 0.1 µg/mL and Ammps was performed to detect the limit of detection in urine (representative of n=3).

Figure 4:
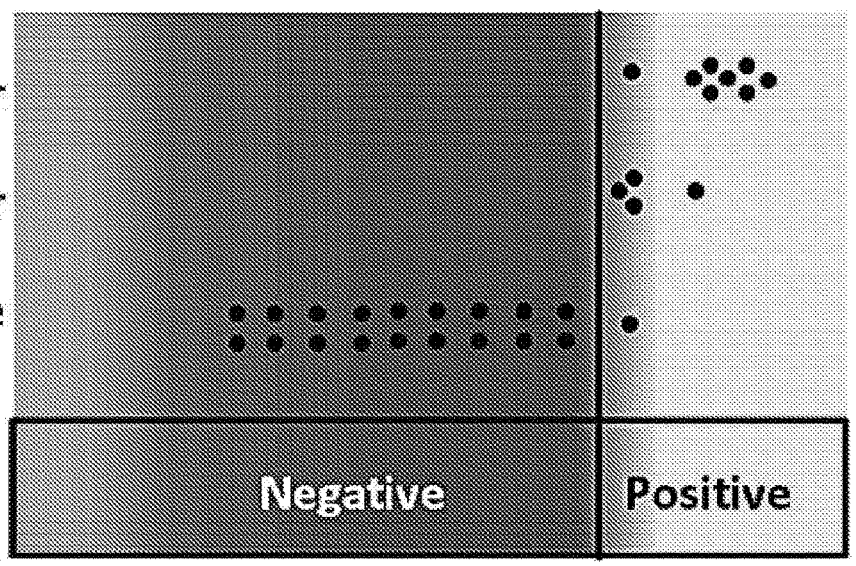

FIG. 4: Ammps have a specificity toward bladder/prostate cancer. Ammps performed on bladder/prostate cancer patients were compared with patients with benign prostatic hyperplasia (BPH) to determine specificity.

Figures 5, 6:
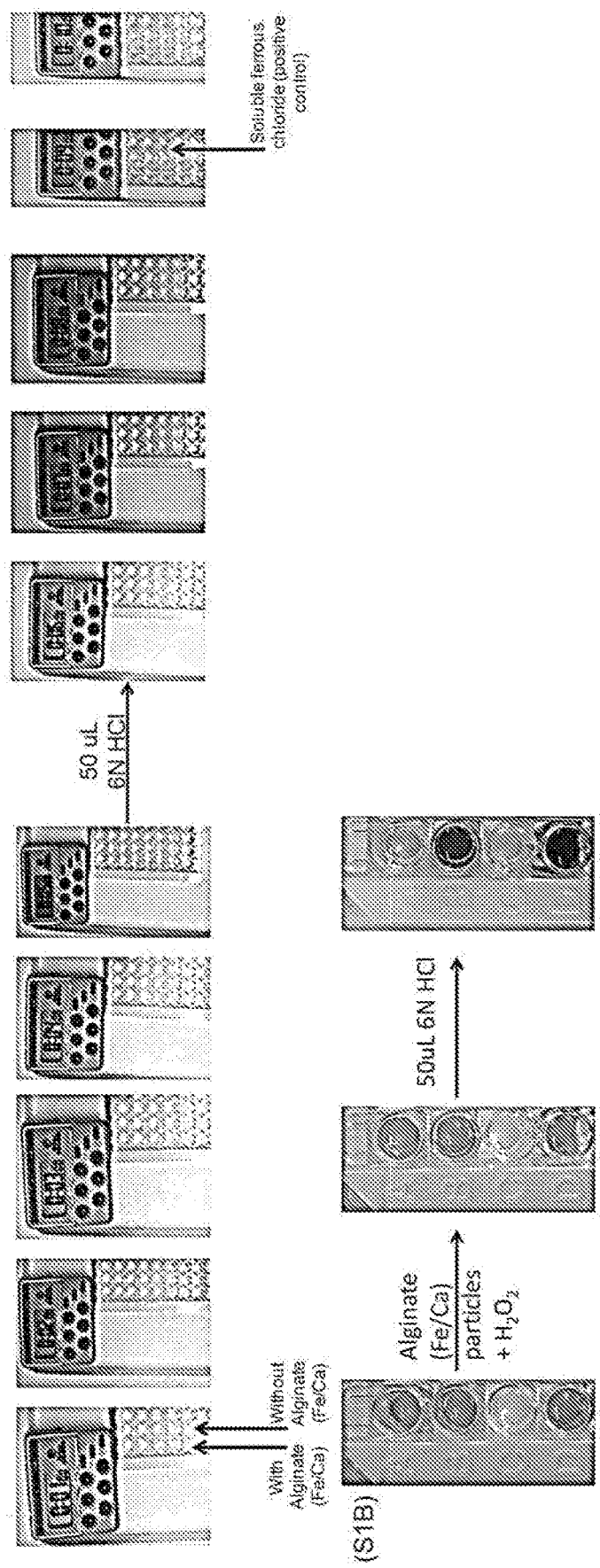

FIG. 5: Photographs of Ammps incubated in presence of a first chromogenic substrate, but no acid, and Ammps incubated in presence of a first chromogenic substrate and HCl.

FIG. 6: Photographs of Ammps incubated in presence of a first chromogenic substrate and a second chromogenic substrate.

Figure 7A:
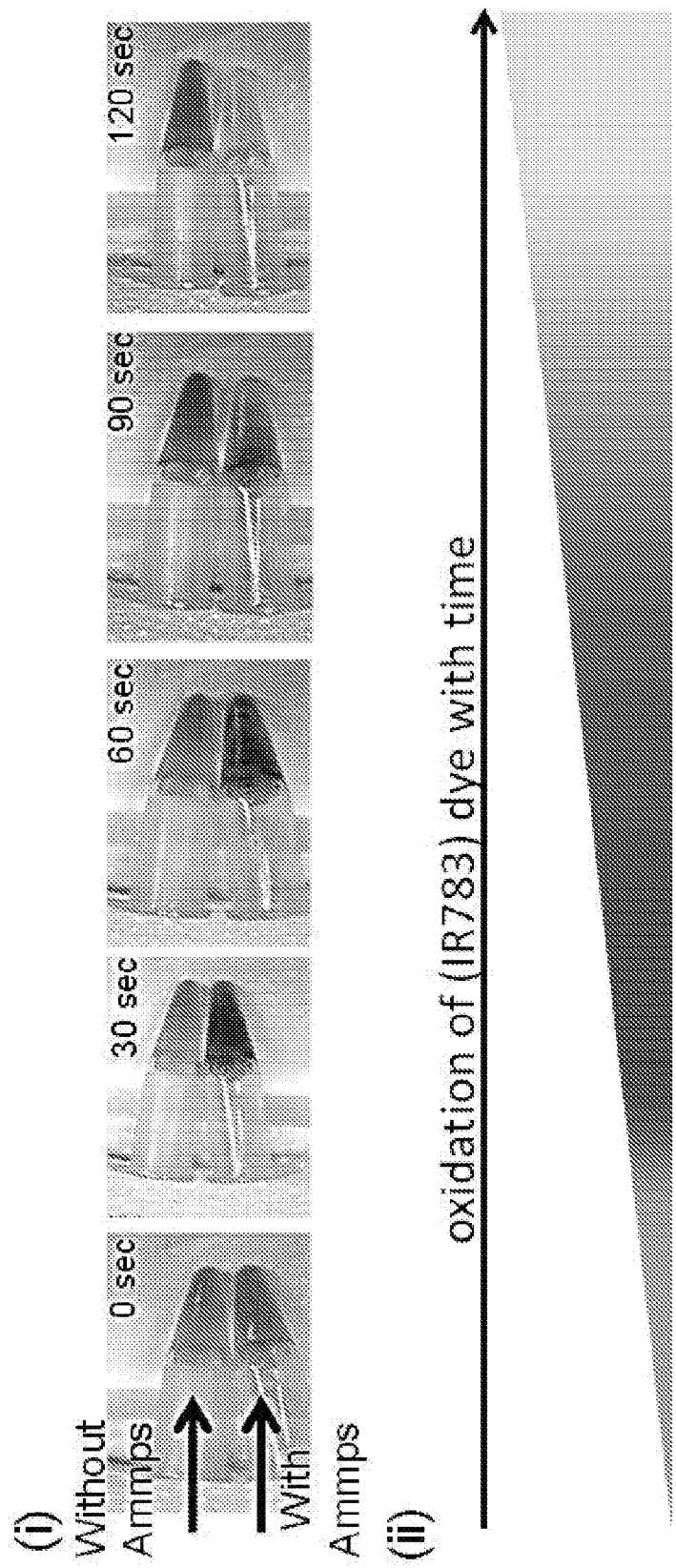

FIGS. 7A-7C. Ammps have a limit of detection of 1 µg/mL in water and urine spiked with collagenase type N. (FIG. 7A) Oxidation of IR783 dyes (i) in the presence or absence of alginate (Fe/Ca) particles (representative of n=3). (ii) Color key for increasing oxidation of IR783 in the presence of Ammps with time is shown. (FIG. 7B) Water was spiked with collagenase type N ranging from 1 µg/mL to 0.1 µg/mL and Ammps was performed to detect the limit of detection in water (representative of n=3). (FIG. 7C) Non-diseased urine was spiked with collagenase type IV ranging from 1 µg/mL to 0.1 µg/mL and Ammps was performed to detect the limit of detection in urine (representative of n=3).

Figure 8:
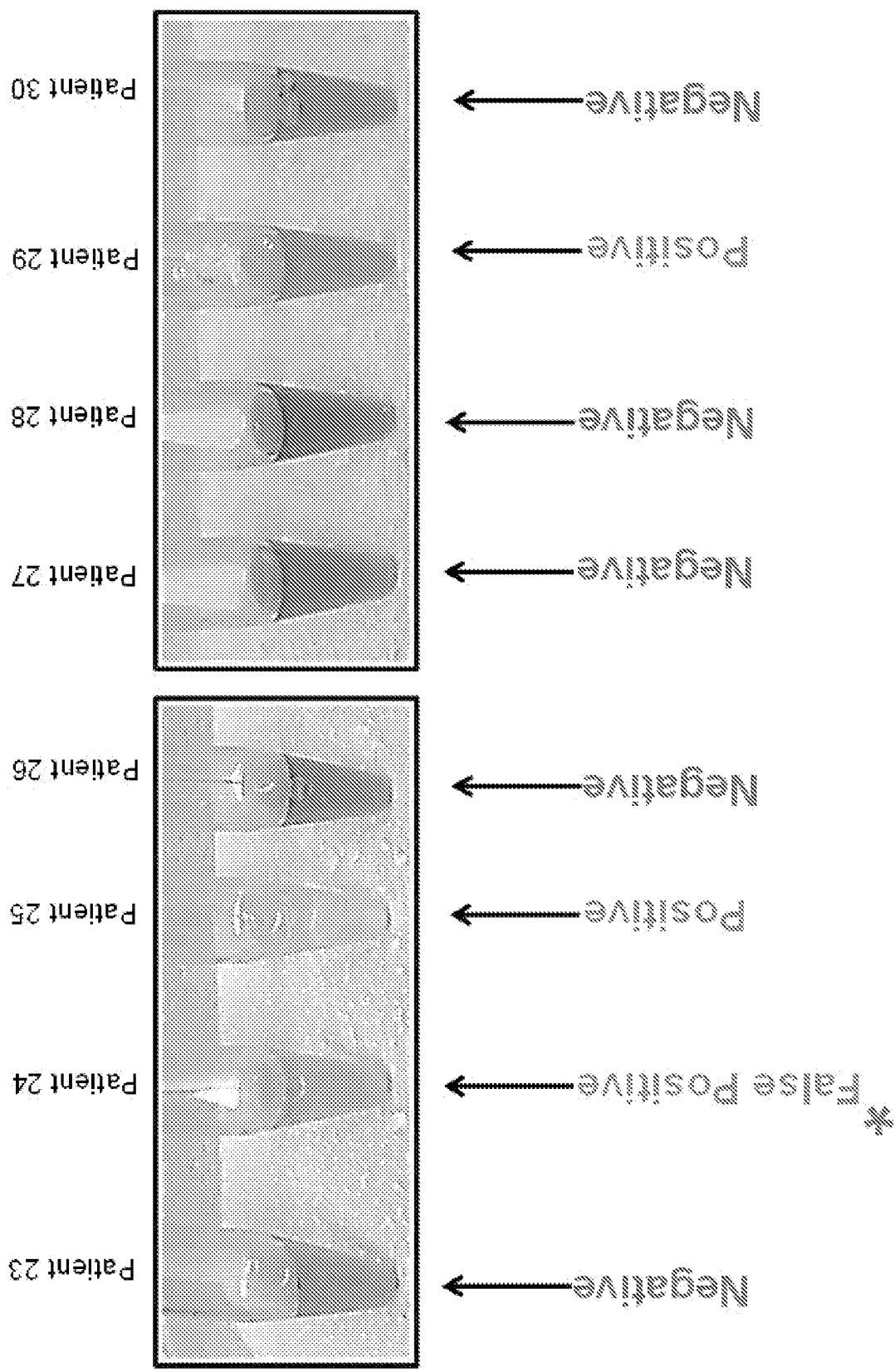

FIG. 8. Ammps identifies patients with bladder cancer. Ammps was performed in a blinded fashion on patients' urine samples and divided into positive (orange-yellow color) and negative (green-purple color) for bladder cancer. Representative images of Ammps performed on patients' urine samples are shown. Code for patients is shown on top and the results are shown on the bottom. * After performing cystoscopy, it was observed that the false positive case had a benign tumor mass.

Figure 9:
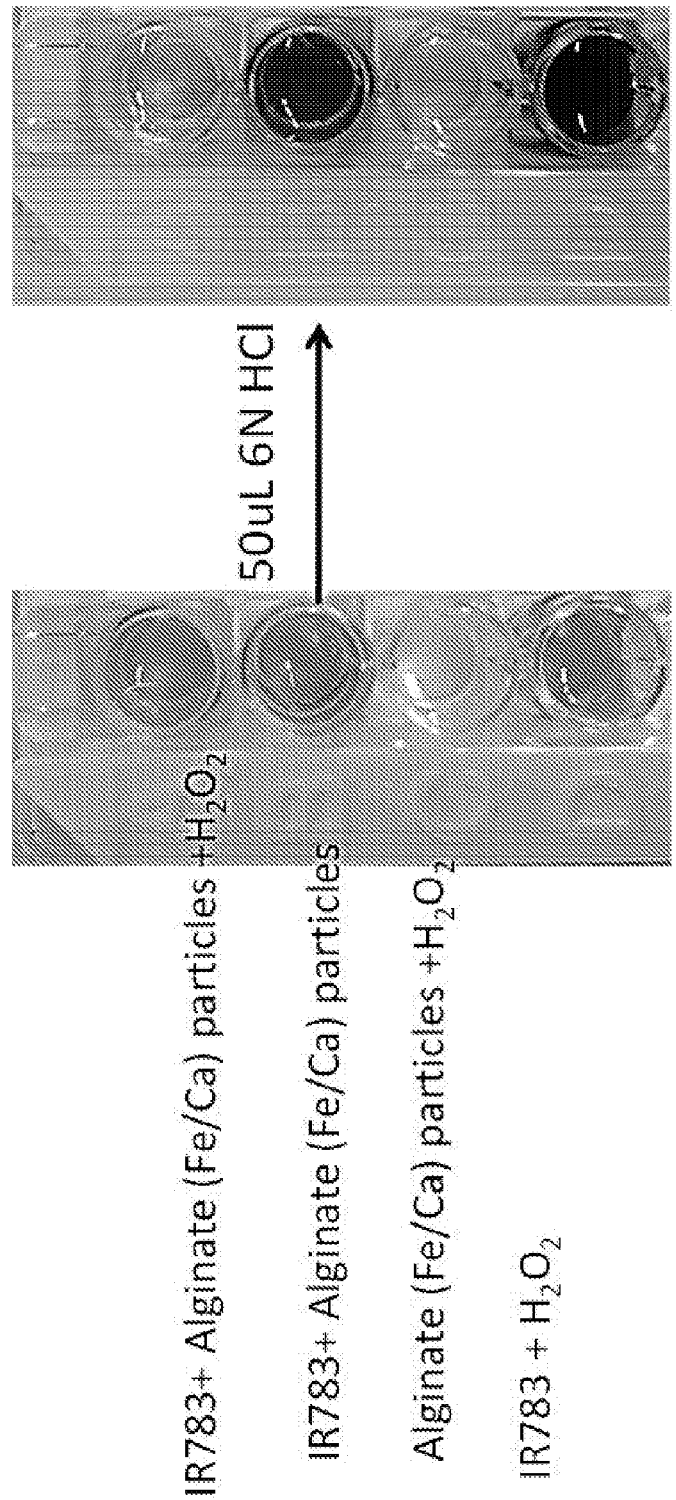

FIG. 9: Gelatin-crosslinked-alginate particles induce color change via Fenton's reaction. Gelatin-crosslinked-alginate particles are able to oxidize IR783 and change their color from green to yellow via Fenton's reaction (representative of n=2) when 6N HCl was added. Moreover, addition of 6N HCl in the absence of Fenton's reaction changes the color of un-oxidized IR783 dye from green to purple.

Figure 10:
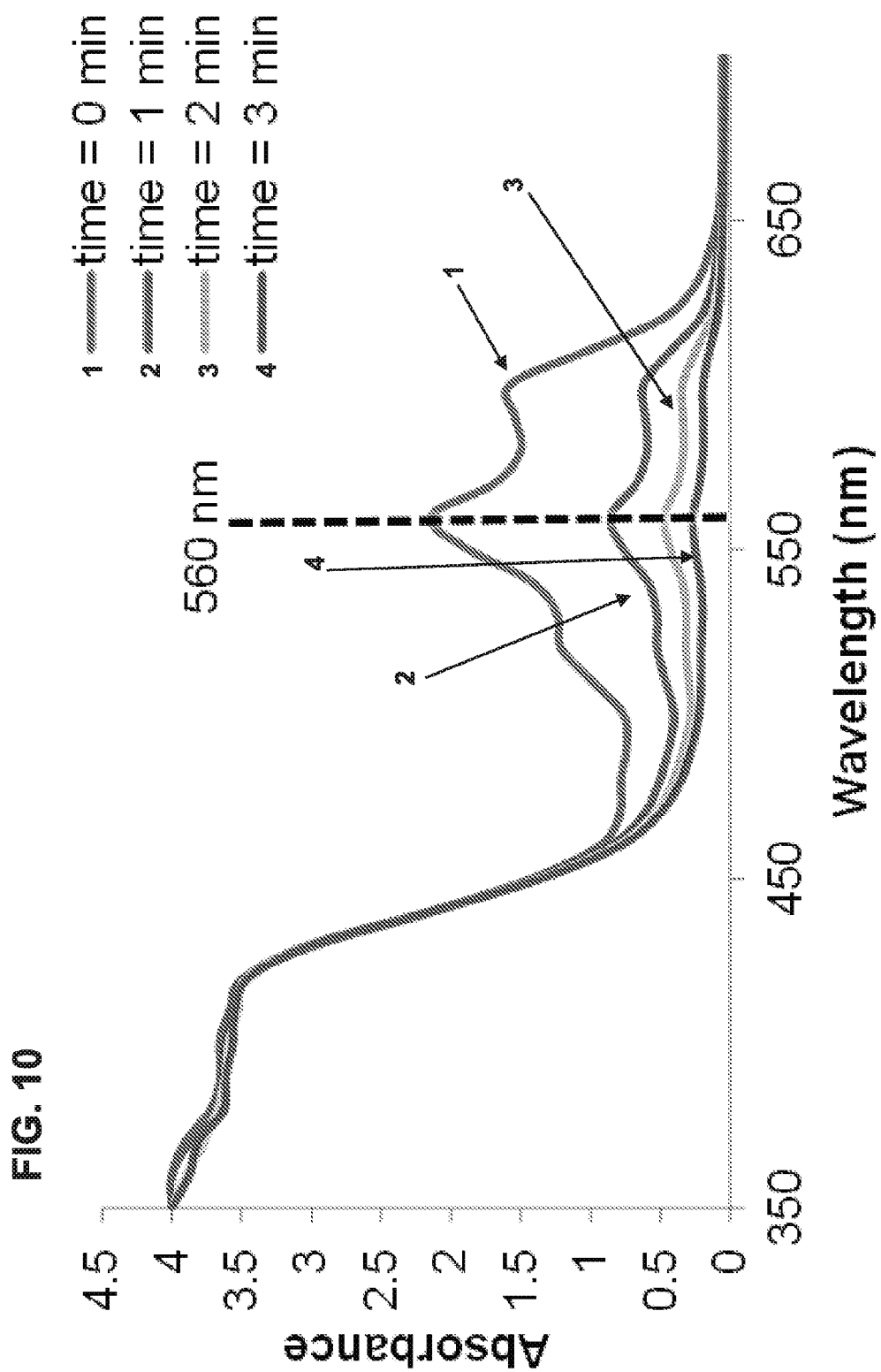

FIG. 10: Absorbance decrease of IR783 with time in the Fenton's reaction. The absorbance of IR783 at 560 nm decreases with time as the reactive oxygen species react generated in the Fenton's reaction degrade the IR783 molecule.

Figure 11:
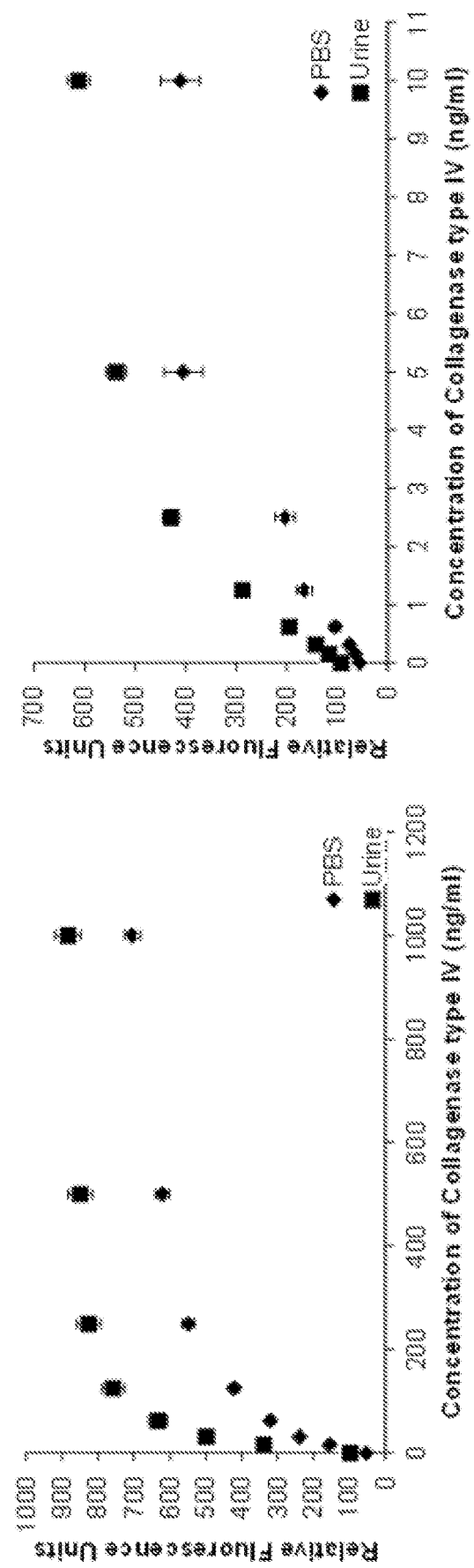

FIG. 11: Detection limit of collagenase type IV in urine and PBS. The activity of collagenase in 30% non-diseased urine sample (in PBS) and in PBS was determined using a substrate of collagenase DQ-FITC. The limit of detection for urine was determined to be 1 ng/mL and in PBS it was determined to be 2 ng/mL.

Figure 12:
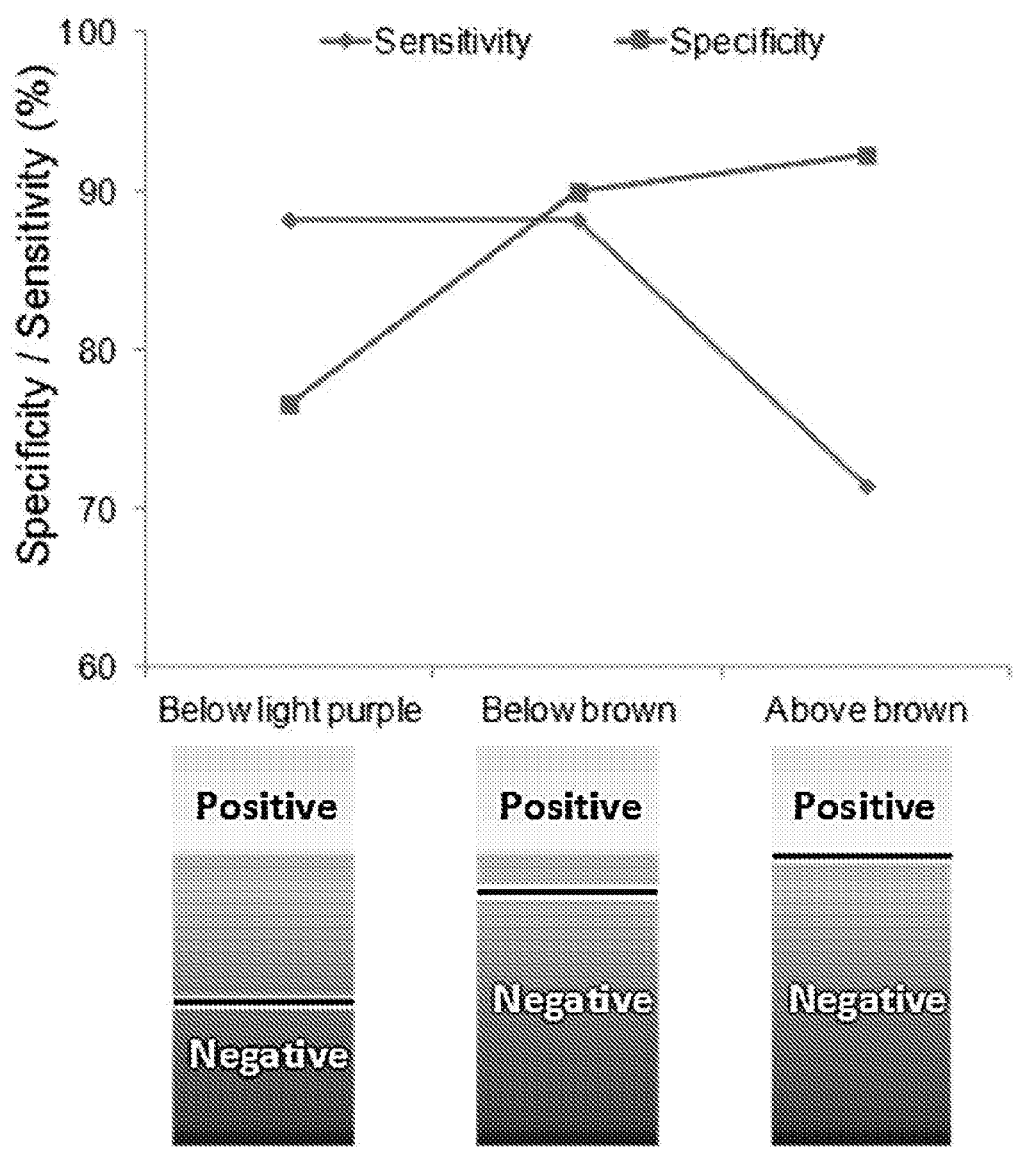

FIG. 12: The cut-off level demarcating negative and positive results from Ammps were determined by optimizing for the highest specificity and sensitivity values. Below the brown color values were chosen to be negative because of the highest sensitivity and specificity at this demarcation.

DETAILED DESCRIPTION

Assays

Bladder and prostate cancer are the most expensive malignancies to treat from diagnosis to death because of the use of regular and expensive send-off lab tests, which are challenging to implement in resource-poor settings. Disclosed herein is an assay for matrix metalloproteinases 2/9 (MMP 2/9) (assay is referred to herein as "Ammp" or "Ammps") that is capable of in-clinic monitoring of the progression of bladder/prostate cancer in resource-poor settings. A visual signal (e.g., a change in color, for example, from purple to yellow) is generated by Ammp, which is based on the gelatinase activity of MMPs on the Ammp substrates. In certain embodiments, Ammp substrates are generated by crosslinking Fe (II) chelated alginate particles and gelatin, and the cleavage of gelatin by gelatinase frees the alginate Fe to generate visual signal via Fenton's reaction. In certain embodiments, Ammps have the limit of detection of 1 µg/mL of gelatinases activity in urine samples and have high specificity toward bladder/prostate cancer. Importantly, Ammps follow the ASSURED guidelines of the World Health Organization and therefore can have an impact in resource-poor settings (see Table 1 below).

TABLE 1

| Affordable | $0.045 per test |
|---|---|
| Sensitive | % |
| Specific | % |
| User-friendly | Utilizes urine (non-invasive). |
| Rapid | Takes less than 30 min including analysis. |
| Equipment free | Visual test. No equipment required. |
| Delivered | No cold-chain required. |

The Ammp assay requires no instruments to measure the signal generated by the active form of MMPs, and therefore, can be utilized in clinics. The Ammp assay detects MMP2/9 in human urine samples within 30 min. and therefore, are useful for in-clinic monitoring or home monitoring of bladder cancer patients or prostate cancer patients, and can potentially be utilized to detect other types of cancers such as breast cancer, brain cancer; renal cancer, and liver cancer among others. Ammp utilize a reaction substrate of gelatinases such as MMP2/9. The Ammp reaction substrate includes gelatin type A crosslinked alginate containing Fe/Ca ions. In certain embodiments, the gelatin type A crosslinked alginate containing Fe/Ca ions is in the form of particles. As used herein, "particle" encompasses spheres, capsules, particles, or rods. The amount of MMP2/9 activity may be compared to collagenase type IV obtained from bovine sources.

Figure 1:
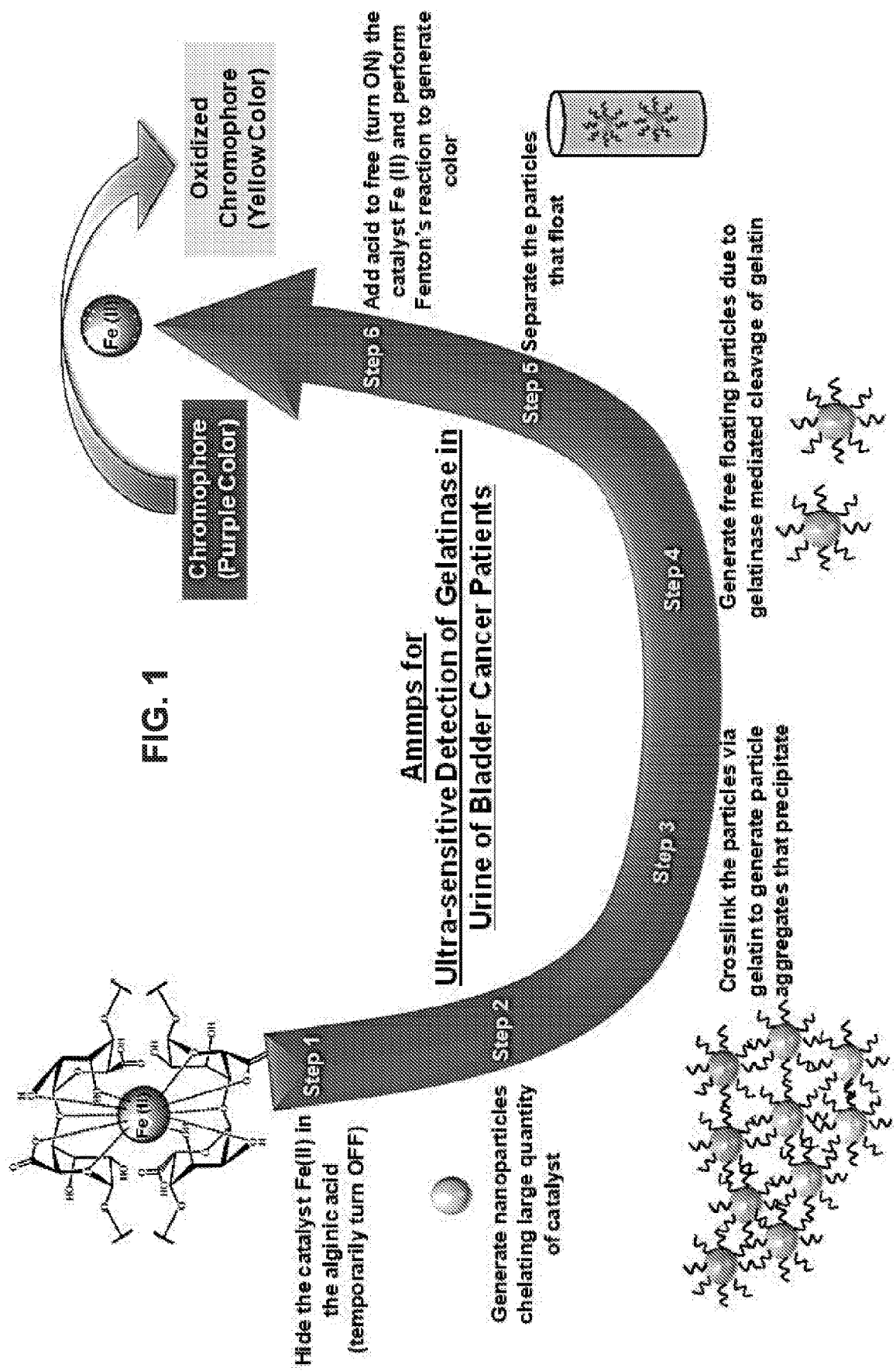
FIG. 1 is a schematic showing the mechanism of detecting gelatinases via an assay for matrix metalloproteinases 2/9 (MMP2/9) (referred to herein as "Ammp"). Step 1. Fe(II), the catalyst for the Fenton's reaction is "hidden" inside the polymer alginate, which chelates Fe(II), and the activity of the catalyst is temporarily turned OFF (Note—$Ca^{+2}$ is also chelated to the alginate but is not shown in FIG. 1). Step 2. Nanoparticles are generated from this chelated Fe(II)-alginate complex with a large quantity of catalyst Fe(II) per nanoparticle. Step 3. These nanoparticles are then precipitated by crosslinking to each other with gelatin as the linker. Step 4. When the precipitated clusters of nanoparticles are exposed to collagenase (active MMPs 2/9) during the assay (such as from urine samples from a bladder cancer patient), the clusters release individual nanoparticles that become re-suspended into the solution. The amount of released individual nanoparticles is proportional to the amount of active MMPs 2/9 Step 5. Next, the re-suspended nanoparticle solution is separated and is added to the chromophore.

Ammps is an assay that is highly sensitive to collagenase activity (observed in urine of bladder cancer patients) because it is able to (a) temporarily turn OFF (hide) the catalytic activity of Fenton's reaction catalyst and (b) turn ON (make available) large quantities of the catalyst in the presence of active collagenase. The mechanism by which Ammp detects MMP2/9 is shown in FIG. 1. Detection of bladder cancer is based on the collagenase activity of active MMPs 2/9 on gelatin-crosslinked-alginate nanoparticles. The Fe(II) catalyst is "hidden" in these alginate nanoparticles through chelation with alginates (steps 1-3). When patient urine is added that contains active MMPs 2/9, alginate nanoparticles are released and re-suspended from the gelatin-crosslinked-alginate aggregates (step 4). The amount of re-suspended nanoparticles generated is proportional to the amount of active MMPs 2/9. This solution of re-suspended particles is then added to the chromophore dye, and Fe (II) is released from the re-suspended alginate nanoparticles by addition of acid (steps 5-6). The chromophore dye becomes oxidized in the presence of Fe (II) via Fenton's reaction and generates a visually observable color (range of color: purple (un-oxidized dye) to yellow (completely oxidized dye), proportional to the amount of active MMPs 2/9).

In certain embodiments, alginate particles were generated using Ca and Fe as the crosslinking agents. These particles were then conjugated with gelatin type A. At room temperature, gelatin coagulates, causing the particles to aggregate. In the presence of gelatinases, gelatin is cleaved thereby generating free floating particles. These free floating particles are isolated, which then initiate Fenton's reaction to generate a color-differentiated product that is visually observed.

The reaction substrate was generated by first forming alginate particles from alginic acid using an inverse emulsion method, with Fe (II) (e.g., from ferrous (II) chloride) and Ca (e.g., from calcium chloride) as the metal ions that are sequestered (e.g., via chelation) by alginic acid. The functional groups of alginic acid that are involved in the chelation are —COOH and —OH groups. Alginates were used as a base material to generate ultra-sensitive substrates for collagenase because of its unique property to chelate divalent cations such as Fe(II) (using —COOH and —OH groups) at a very high density. This is advantageous because a large amount of Fe (II) will lead to faster reaction and rapid generation of a large amount of reaction product (color). In certain embodiments, the cation density can range from 0.001 mg to 10 mg, whereas the particle density can range from 2 particle to 1,000,000,000 particles.

The alginate particles may be formed by contacting an alginic acid with a Fe(II) ion source and, optionally, a $Ca^{+2}$ ion source. Illustrative Fe(II) ion sources include iron oxide, iron chloride, iron phosphate, iron (II) sulfate, ammonium iron sulfate, dichlorotetrakis(pyridine)iron, iron bromide, iron citrate, iron fluoride, iron iodide, iron molybdate, iron nitrate, iron oxalate, iron perchlorate, iron phosphate, iron pyrophosphate, iron tetrafluoroborate, potassium hexacyanoferrate(II), among others in different hydration states. Illustrative $Ca^{+2}$ ion sources include calcium chloride, calcium carbonate, calcium acetate, calcium citrate, calcium sulfate, calcium pyrophosphate, calcium propionate, calcium phosphate, calcium oxide, calcium oxalate, calcium lactate, calcium hydroxide, calcium gluconate, calcium glubionate, among others in different hydration states. Alginate particles can be made with only chelated Fe(II), but the yield may be too low. $Ca^{+2}$ provides better binding to alginate than Fe, and thus is used in conjunction with Fe(II). However, the $Ca^{+2}$ does not participate in the Fenton's reaction.

All forms of alginic acid or alginate can be used to generate the particles. These include alginates with medium or low viscosity and alginic acid at different forms of purification from algae. Moreover, alginic acid can be in the form of salts such as sodium among others that can also be used to generate alginate particles. Alginic acid provides a dual advantage of the capability (1) of generating particles and (2) chelating Fe and Ca ions.

In certain embodiments, the inverse emulsion may be a water-in-oil emulsion. An aqueous solution of alginic acid is prepared. This solution of alginic acid (which constitutes the water phase) is added to an oil phase. Illustrative oils for the oil phase include alkanes or substituted alkanes such as octane, isooctane, dichloromethane, ethyl acetate, dimethylformamide, hexanes, ether, or chloroform, aromatics such as toluene, and combinations thereof. The Fe(II) ion source and the $Ca^{+2}$ ion source are added to the resulting alginic acid/oil mixture thus forming a water-in-oil emulsion. For example, the composition of the dispersed phase may be water (100 uL to 100 mL), a water soluble detergent that can be Triton x-100, Tween 20, Tween 80, or Pluronics among others (100 uL to 100 mL of 0.1-10% wt/wt), alginic acid (0.1 mg to 100 mg), and the Ca and Fe ions (0.1 mg to 100 mg). The continuous phase may include the oil (such as octane (1 mL to 1000 mL)) and oil soluble detergents such as Brij30, Brij 35, Brij 56, Brij 58, or Span 80 among others (100 uL to 100 mL of 0.1-10% wt/wt). Next isopropanol (1 ml to 10000 mL) is added to cure the particles. Other curing agents such as various alkanols such as methanol, ethanol among others can be used as well. Next the particles thus formed are precipitated by centrifuging in a centrifuge for certain amount of time (1,2,3,4,5,10,20,30 minutes) at (1,5, 10,20,30,40,50,100×G force) to isolate the particles. These particles are then freeze dried and used.

In certain embodiments, the resulting alginate (Fe/Ca) particles have an average particle size of at least 800 nm, more particularly at least 1000 nm. In certain embodiments, the resulting particles have an average particle size of not greater than 5000 nm, more particularly not greater than 1000 nm.

The particles may be activated to provide functional groups on the particles for conjugating with a gelatinase-specific gelatin-type substrate. Particle activation may be accomplished by contacting the particles with an activating agent such as glutaraldehyde, paraformaldehyde, formaldehyde, Ethyl-3-(3-dimethylaminopropyl)-carbodiimide), Sulfo-N-hydroxysulfosuccinimide, N-hydroxysuccinimide, Azabenzotriazole-1-yl)-N,N,N,N'-tetramethyluronium hexafluorophosphate, (2-(1H-benzotriazol-1-yl)-1,1,3, 3-tetramethyluronium hexafluorophosphate), and O-(Benzotriazol-1-yl)-N,N,N',N'-tetramethyluronium tetrafluoroborate among others.

The activated particles may be conjugated to gelatinase-specific gelatin-type substrate by reacting or contacting the particles with a gelatinase-specific gelatin-type substrate. Gelatinase-specific gelatin-type substrates include, but not limited to, materials that can be converted into gelation (e.g., collagen) and material that constitute a part of the extracellular matrix (e.g, fibronectin). Illustrative gelatinase-specific gelatin-type substrates include gelatin A, gelatin B, mixed gelatin, collagen type I, III, IV, V, VII and X, fibronectin, laminin, aggrecan, link protein, elastin, vitronectin, tenascinp, SPARC, decorinr, myelin basic protein, α1Pls, α1-antichymotrypins, IL-1beta, proTNF-α, IGFBP-β, substance P, casein, and similar materials. In certain embodiments, gelatin type A (0.001 mg to 10 mg) was used to conjugate to alginate particles (0.01 mg to 100 mg). The functional group of alginate that is conjugated is —COOH and —OH groups, whereas the functional group of —NH$_2$ and —COOH are conjugated on the gelatin. In certain embodiments, in order to generate nanoparticles containing Fe (II) that are sensitive to collagenase activity, alginate particles may be crosslinked to each other with gelatin type A (a substrate of collagenase) as a linker. This crosslinking may be achieved by first activating the alginate particles with EDC/sulfo-NHS. Next, the EDC/sulfo-NHS is removed, and gelatin is added to the particles (incubated for 16 hours) to generate inter-crosslinked structures that would precipitate in solution.

In certain embodiments, the resulting alginate (Fe/Ca)—gelatin conjugated particles have an average particle size of at least 0.005 mm, more particularly at least 0.01 mm. In certain embodiments, the resulting particles have an average particle size of not greater than 0.10 mm, more particularly not greater than 0.01 mm.

The alginate (Fe/Ca)—gelatin conjugated particles are contacted (e.g., mixed) with a biological sample (e.g., urine, blood, plasma or serum) from a subject. If gelatinase activity (e.g., MMP2 and/or MMP 9) is present in the biological sample, the enzyme cleaves the gelatin from the particles, thus freeing the alginate particles containing Fe (II) and Ca(II) ions.

At least a portion of the biological sample that includes the alginate (Fe/Ca)—gelatin conjugated particles is contacted (e.g., mixed) with a Fenton reaction substrate composition. The Fenton reaction substrate composition includes a Fenton reagent and at least one chromogenic substrate that changes color in the presence of the Fenton reagent. In certain embodiments, the Fenton reaction substrate composition includes H$_2$O$_2$ (e.g., 0.0001 M to 8 M), HCl (e.g., 0.05 N to 6 N), at least one first chromogenic substrate that changes color from transparent to yellow, and at least one second chromogenic substrate that changes color from purple to yellow. In certain embodiments, HBr or H$_2$S could be substituted for HCl. Fenton's reaction generates radical oxygen species such as hydroxyl radicals and singlet radical oxygens that then oxidize the first chromogenic substrate (initially transparent) causing the change in its structure, generating a pi-pi conjugation structure thereby generating a color (purple, which in the presence of Ammp substrates turns yellow). The second chromogenic substrate also gets oxidized by the radical oxygen species that causes it to change its color from purple to yellow. In certain embodiments, Fenton reaction substrate composition includes a Fenton reagent and at least one chromogenic substrate that changes it color from purple to yellow. In certain embodiments, Fenton reaction substrate composition includes a Fenton reagent and a single chromogenic substrate, wherein the single chromogenic substrate is the second chromogenic substrate (e.g., the second chromogenic substrate as described below, or a similar second chromogenic substrate)

Illustrative first chromogenic substrates include those having the structure of:

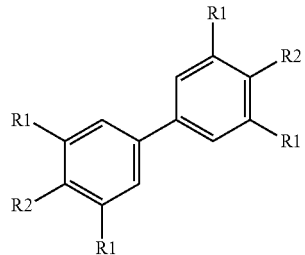

wherein each R1 is independently selected from —CH$_3$, =CH$_2$, ≡CH, —OH, or —NH$_2$; and each R2 is independently selected from —NH$_2$, —OH, or —COOH. An illustrative first chromogenic substrate is 5,5'-Tetramethylbenzidine (TMB)

Illustrative second chromogenic substrates include 2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, inner salt sodium salt (IR783), and compounds having a structure of:

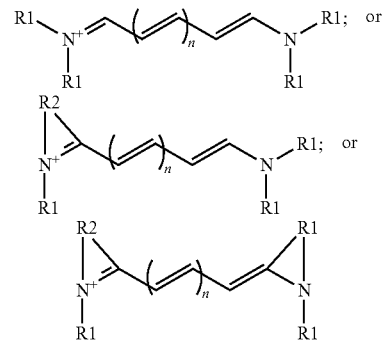

wherein n=1 to 7; and each R1 is independently an alkyl, substituted alkyl, aryl, or substituted aryl; and each R2 forms part of a ring, particularly an aromatic ring such as pyrrole, indole or pyridine.

The alkyl may be a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or (C$_1$-C$_6$)alkyl can be methyl, ethyl, propyl, isopropyl, butyl, iso-butyl, sec-butyl, pentyl, 3-pentyl, or hexyl; (C$_3$-C$_6$) cycloalkyl can be cyclopropyl, cyclobutyl, cyclopentyl, or cyclohexyl; (C$_3$-C$_6$)cycloalkyl(C$_1$-C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$-C$_6$)alkoxy can be methoxy, ethoxy, propoxy, isopropoxy, butoxy, iso-butoxy, sec-butoxy, pentoxy, 3-pentoxy, or hexyloxy; (C$_2$-C$_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2\text{-}C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1\text{-}C_6)$alkanoyl can be acetyl, propanoyl or butanoyl; halo$(C_1\text{-}C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1\text{-}C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1\text{-}C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1\text{-}C_6)$alkylthio can be methylthio, ethylthio, propylthio, isopropylthio, butylthio, isobutylthio, pentylthio, or hexylthio; $(C_2\text{-}C_6)$alkanoyloxy can be acetoxy, propanoyloxy, butanoyloxy, isobutanoyloxy, pentanoyloxy, or hexanoyloxy.

The aryl may be a monovalent unsaturated aromatic carbocyclic group having a single ring (e.g., phenyl) or multiple condensed rings (e.g., naphthyl or anthryl), which can optionally be unsubstituted or substituted.

Other chromogens can be used for the second chromogenic substrate such as ICG, IR780, cyanine 2, cyanine 2.5, cyanine 5, and cyanine 7. Other chromogens can be used for the first chromogenic substrate such as, paranitrophenol, (2,2-Azinobis [3-ethylbenzothiazoline-6-sulfonic acid]-di-ammonium salt), (o-phenylenediamine dihydrochloride), (o-nitrophenyl-β-D-galactopyranoside), CN (4-chloro-1-naphthol) and DAB (3,3'-diaminobenzidine tetrahydrochloride) among others.

In certain embodiments, the color change that occurs over time in the presence of gelatinase is from green to blue to purple to orange to yellow. The color change can be visually detected by an un-aided human eye. The color change can also be read and recorded on a spectrophotometer.

Detecting the presence of, or an alteration in the amount of, one or more of the proteins using the methods disclosed herein indicates the prognosis or diagnosis of the subject, or indicates if a therapy is effective for treating a subject.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

Kits are also provided. The kit can include the alginate (Fe/Ca)—gelatin conjugated particles, and optionally the Fenton reaction substrate composition. The kit can include a container and a label or package insert on or associated with the container. Suitable containers include, for example, bottles, vials, syringes, etc. The containers may be formed from a variety of materials such as glass or plastic. The container typically holds a composition including one or more of the particles. In several embodiments the container may have a sterile access port.

A label or package insert indicates that the composition is of use for evaluating the presence or progression of cancer, particularly bladder cancer or prostate cancer in a subject. The label or package insert typically will further include instructions for use, such as particular assay conditions. The package insert typically includes instructions customarily included in commercial packages of products that contain information about the indications, usage, contraindications and/or warnings concerning the use of such products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a color change (e.g. a color comparison guide). The kits may additionally include buffers and other reagents routinely used for the practice of a particular method.

Several embodiments are disclosed in the following numbered, clauses:

1. A Fe(II)- and $Ca^{+2}$-chelated alginate/gelatin conjugate.
2. The conjugate of clause 1, wherein the gelatin is gelatin A.
3. The conjugate of clause 1 or 2, wherein the conjugate is in the form of a particle.
4. The conjugate of any one of clauses 1 to 3, wherein the gelatin is a gelatinase-specific gelatin-type substrate selected from gelatin A, gelatin B, mixed gelatin, collagen type I, III, IV, V, VII and X, fibronectin, laminin, aggrecan, link protein, elastin, vitronectin, tenascinp, SPARC, decorinr, myelin basic protein, α1Pls, α1-antichymotrypins, IL-1beta, pro-TNF-α, IGFBP-β, substance P, or casein.
5. A composition comprising the conjugate of any one of clauses 1 to 4.
6. The composition of clause 5, wherein the composition includes a plurality of conjugate particles.
7. The composition of clause 6, wherein the particles have an average particle size of at least 100 nm, more particularly at least 800 nm.
8. The composition of clause 6 or 7, wherein the particles have an average particle size of not greater than 1000 nm, more particularly not greater than 800 nm.
9. The composition of any one of clauses 5 to 8, wherein the composition is in the form of a bioassay.
10. A kit comprising:
    the composition of any one of clauses 5 to 8; and
    a composition comprising a Fenton reagent and at least one chromogenic substrate.
11. The kit of claim 10, wherein the composition comprising a Fenton reagent and at least one chromogenic substrate comprises $H_2O_2$, HCl, at least one first chromogenic substrate, and at least one second chromogenic substrate.
12. A method for detecting the presence of cancer in a subject, comprising:
    contacting a biological sample from the subject with the conjugate of any one of clauses 1 to 3 to form a sample/conjugate composition; and
    contacting the sample/conjugate composition with a composition that comprises a Fenton reagent and at least one chromogenic substrate resulting in an assay composition;
    wherein detection of a color change in the assay composition indicates the presence of a matrix metalloproteinase in the biological sample.
13. The method of clause 11, wherein the composition comprising a Fenton reagent and at least one chromogenic substrate comprises $H_2O_2$, HCl, at least one first chromogenic substrate, and at least one second chromogenic substrate.
14. The method of clause 12 or 13, wherein the conjugate is in the form of a particle.
15. The method of any one of clauses 12 to 14, wherein the matrix metalloproteinase is matrix metalloproteinase 2, matrix metalloproteinase 9, or both matrix metalloproteinase and matrix metalloproteinase 9.

16. The method of any one of clauses 12 to 15, wherein the cancer is prostate cancer or bladder cancer.

17. The method of any one of clauses 12 to 15, wherein the cancer is prostate cancer.

18. The method of any one of clauses 12 to 15, wherein the cancer is bladder cancer.

19. The method of any one of clauses 12 to 18, wherein the cancer can be distinguished from benign prostate hyperplasia.

20. The method of any one of clauses 12 to 18, wherein the cancer can be distinguished from benign conditions causing hematuria.

Example 1

Ammp substrate: An inverse emulsion of water in octane was utilized to generate particles. A 10 mg/mL solution of alginic acid (Fisher Scientific, Pittsburgh, Pa.) in DI $H_2O$ was generated and used as the water phase. Span 80 (1.25 mL; Fisher Scientific) was dissolved in 75 mL of octane (Fisher Scientific, Pittsburgh, Pa.), and used as the, oil phase. This solution of alginic acid was then added to the oil phase under stirring at 7,000 rpm (Silverson L4RT-A, East Longmeadow, Mass.) and allowed to mix for 3 min. 35 mL of 700 mM $CaCl_2$ solution and 35 mL of 700 mM ferrous (II) chloride tetrahydrate (Fisher Scientific, Pittsburgh Pa.) solution made in DI $H_2O$ was then added under stirring at 7,000 rpm and allowed to mix for 3 min. 2-propanol (100 mL; Fisher Scientific, Pittsburgh Pa.) was then added to the mixture in order to cure the particles, and allowed to mix for 3 min. During the process of curing the particles are stabilized and the detergent that covers the particles is removed. The particles obtained were centrifuged (Eppendorf) at 2000×Gs for 2 min and the supernatant was discarded. The particles were then re-suspended in 2-propanol, incubated at room temperature for 5 min and then centrifuged again at 2000×Gs for 2 min. The alginate particles were then lyophilized and used for further experiments.

The resulting particles were imaged using a scanning electron microscope (SEM) and the average size of particles was observed to be 900 nm using dynamic light scattering (DLS) (FIG. 2A).

10 mg of alginate particles were re-suspended in 0.9 mL of $DIH_2O$ and 0.1 mL of 25% glutaraldehyde (Sigma-Aldrich, St. Louis, Mo.) was added to the solution. This solution was incubated at room temperature for 5 min. Next, the particles were washed 3 times to remove excess glutaraldehyde by centrifuging at 2000× for 5 min and re-suspending them in fresh 1 mL $DIH_2O$. The approximate number of particles was calculated from the average diameter of particles 800 nm and alginic acid density of 1.6 g/cm$^3$. Two equivalents of gelatin type A (Bloom 225, Fisher Scientific, Pittsburgh Pa.; re-suspended at 1 mg/mL in $DIH_2O$ at 37° C.) was added to the particles. The reaction was carried out for 16 h under stirring, at 37° C. The particles thus formed were centrifuged washed 3 times at 2000× for 5 min using $DIH_2O$ at 37° C. These particles were then lyophilized and used as is.

The amount of gelatin per mg of particles was determined using BCA analysis to be 192±42 µg/mg. The resultant crosslinked particles were then imaged using SEM and it was observed that the particles were now agglomerated as compared to the non-conjugated particles (FIG. 2B). This agglomeration was further confirmed by sizing the particles using DLS, where the size of the aggregates was observed to be 2-6 µm (FIG. 2C). Next, it was determined if the size of particles is modified in the presence of collagenases activity. 1 mg/mL collagenase type IV in 500 µL PBS was incubated with 50 µL of Ammp substrates (3 mg/mL) for 25 min and the size of the particles was measured using DLS at 25 min post incubation. It was observed that the size of the particles decreased from 2-6 µm to 500 nm.

Fenton's reaction substrate: Fenton's reaction substrate consisted of 100 µL 6N HCl (Fisher Scientific, Pittsburgh Pa.), 100 µL TMB substrate (R&D Systems, Minneapolis, Minn.), 100 µL $H_2O_2$ (R&D Systems, Minneapolis, Minn.) and 10 µL of 1 mg/mL IR783 in $DIH_2O$ (Sigma Aldrich, St. Louis, Mo.). Urine collection: All the protocols utilized here for collecting urine from patients were approved by the IRB committee of the Human Research Protection Office of University of Pittsburgh. The urine was collected at UPMC Mercy Hospital and utilized on the same day.

In order to determine if the Ammp substrates perform Fenton's reaction and generate visual color, Ammp substrate 50 uL (3 mg/mL) in $DIH_2O$ was incubated in the presence of TMB substrate and the change in color was noted. It was observed that even after 5 min of incubation no color was generated (FIG. 5). Using these data we hypothesized that the Fe chelated by carboxyl and hydroxyl groups in the alginate particles were not able to participate in the Fenton's reaction. Therefore, 50 µL of 1 N HCl was added to the reaction mixture in order to release Fe from alginate particles and the reaction was carried out. It was observed that within 5 min a yellow color was generated which is typically observed due to oxidation of TMB (FIG. 5). Soluble 0.1 mg/ml ferrous chloride incubated with the TMB and $H_2O_2$ was utilized as the positive control, which showed immediate generation of yellow color. Moreover, since, the Ammps need to be able to detect MMP2/9 in the urine samples (transparent to yellow colored), it is of great benefit if the starting color of the Ammp substrate was different than yellow. Therefore, we added another substrate of the Fenton's reaction, IR783, which turns from green to transparent in the presence of reactive oxygen species generated in the reaction (FIG. 6). Next the range of color change that occurred in the presence of Ammp substrate and TMB+ IR783 was tested. FIG. 3A demonstrates that in the presence of Ammp substrate the color changes from green—blue—purple—yellow with time. This change is depicted in the form of a gradient for reference (FIG. 3B).

Next, it was determined if Ammp could detect collagenase in phosphate buffered saline (PBS). 1 mL of PBS was spiked with collagenase type IV to generate 1 µg/ml, 1 ng/ml, 100 µg/ml, 10 µg/ml, 1 µg/ml and 0.1 µg/ml concentrations in 1.5 mL Eppendorf tubes. A 50 µL of Ammp substrate was added to the PBS and incubated at room temperature for 25 min. Next, 300 µL of the solution was retrieved without disturbing the Eppendorf tube and added to another tube containing HCl. IR783, TMB, and $H_2O_2$ were then added to this Eppendorf tube. The change in color was observed for 3 min and a photograph was obtained using a camera phone. It was observed that Ammps were able to change the color of the solution from purple to yellow (purple=negative; yellow=positive) so as to differentiate between 1 µg/mL and 0 µg/mL of collagenase type, IV in PBS (FIG. 3B). Similarly, Ammps was tested to determine whether it could detect collagenase type IV in human urine samples. Non-diseased urine sample was spiked with collagenase type IV to generate 1 mg/ml, 1 ng/ml, 100 µg/ml, 10 µg/ml, 1 µg/ml, 0.1 µg/mL and 0.01 µg/ml concentrations in 1.5 mL Eppendorf tubes. A 0.3 mL of the urine, 0.7 mL of 10×PBS and 50 µL of Ammp substrate was reacted for 25 min and 0.3 mL of the solution was retrieved without disturbing the Eppendorf tube and added to another tube containing HCl, after which IR783, TMB, and $H_2O_2$ were added. It was observed that Ammps were able to differentiate between 1 μg/mL and the negative control of 0 μg/mL of collagenase type IV with naked eye (FIG. 3C).

In order to determine if the Ammps could be used for detecting collagenase in the urine samples of bladder/prostate cancer patients, urine samples from a clinic were obtained and Ammps was performed on the samples in a blinded fashion. Patients' samples were coded with patient's initials and the date the samples were donated. A total of 26 patients were tested for the presence of collagenase type N in the urine of patients. The urine was collected from patients and utilized fresh within 1 h. 50 μL of Ammp substrate (3 mg/mL in PBS), 0.3 mL of the urine and 0.7 mL of 10×PBS was added in an Eppendorf tube and allowed to react for 25 min. Next 0.3 mL of this reaction mixture was pipette out into another Eppendorf tube containing IR783, TMB, HCl and $H_2O_2$. The color of the solution at the end of 3 min was noted and plotted on a graph y-axis representing different colors of the solution and the patient code on the x-axis (FIG. 4A). It was observed that a total, of 14 patients were positively identified as being positive for bladder cancer using Ammps and 12 patients negative for bladder cancer using Ammps. There were 11 true positives, 19 true negatives, 1 false positive and 0 false negative for bladder and prostate cancer. Also the Ammps were able to distinguish between patients with hematuria with bladder cancer and hematuria without bladder cancer with 100% specificity and sensitivity.

Example 2

Ammps substrate: An inverse emulsion of water in octane was utilized to generate nanoparticles. A 10 mg/mL solution of alginic acid (Fisher Scientific, Pittsburgh, Pa.) in DI $H_2O$ was generated and used as the water phase. Span 80 (1.25 mL; Fisher Scientific) was dissolved in 75 mL of octane (Fisher Scientific, Pittsburgh, Pa.), and used as the oil phase. This solution of alginic acid was then added to the oil phase under stirring at 7,000 rpm (Silverson L4RT-A, East Longmeadow, Mass.) and allowed to mix for 3 min. Thirty-five (35) mL of 700 mM CaCl2 solution and 35 mL of 700 mM ferrous (II) chloride tetrahydrate (Fisher Scientific, Pittsburgh Pa.) solution made in DI $H_2O$ was then added under stirring at 7,000 rpm and allowed to mix for 3 min. One hundred (100) mL of 2-propanol (Fisher Scientific, Pittsburgh Pa.) was then added to the mixture in order to cure the particles, and allowed to mix for 3 min. The particles obtained were centrifuged (Eppendorf) at 2000×Gs for 2 min and the supernatant was discarded. The particles were then re-suspended in 2-propanol, incubated at room temperature for 5 min and then centrifuged again at 2000×Gs for 2 min. The alginate particles were then lyophilized and used for further experiments.

Ten (10) mg of alginate particles were resuspended in 0.9 mL of $DIH_2O$ and 0.1 mL of 20 mg EDC (1-ethyl-3-(3-dimethylaminopropyl)carbodiimide hydrochloride and 25 mg sulfo-NHS (N-hydroxysulfosuccinimide) (Sigma-Aldrich, St. Louis, Mo.) was added to the solution. This solution was incubated at room temperature for 25 min. Next, the particles were washed 3 times to remove excess EDC/sulfo-NHS by centrifuging at 2000× for 5 min and resuspending them in fresh 1 mL $DIH_2O$. The approximate number of particles was calculated from the average diameter of particles 700 nm and alginate density of 1.6 g/cm³, and 2 mole excess of gelatin type A to number of particles (Bloom 225, Fisher Scientific, Pittsburgh Pa.; re-suspended at 1 mg/mL in $DIH_2O$ at 37° C.) was added to the particles. The reaction was carried out for 16 h under stirring at 37° C. The particles thus formed were centrifuged and washed 3 times at 2000× for 5 min using $DIH_2O$ maintained at 37° C. Fenton's reaction substrate: Fenton's reaction substrate consisted of 100 μL 6N HCl (Fisher Scientific, Pittsburgh Pa.), 100 μL $H_2O_2$ (R&D Systems, Minneapolis, Minn.) and 10 μL, of 5 mg/mL IR783 in $DIH_2O$ (Sigma Aldrich, St. Louis, Mo.). First the 0.3 mL of sample that had been incubated with Ammps for 25 min, was added to the 100 μL 6N HCl in an eppendorf tube. Next, 10 μL of IR783 and 100 μL, $H_2O_2$ were added in this sequence. The reaction was carried out for 3 min and a camera was utilized to image the color generated.

Urine collection and clinical data: All the protocols for urine collection were approved by the IRB committee of the Human Research Protection Office of University of Pittsburgh. The experiments were performed in a blinded fashion.

The results of Example 2 are shown in FIGS. 7-12.

The patients that were positive for cancer via conventional screening methods of cystoscopy, Gleason score and urine analysis were identified. Patients that had benign prostate hyperplasia were also identified using these tests. In order to determine specificity and sensitivity of Ammps, the false positive (FP) and false negative (FN) of the Ammps for detecting bladder cancer in patients was determined. FP and FN were determined by comparing the data obtained from Ammps with these conventional tests. Specificity and sensitivity were determined using the formulae:

Specificity=Number of true negatives/number of true negatives+number of false positives $$\text{Specificity} = \frac{\text{Number of true negatives}}{\text{number of true negatives} + \text{number of false positives}}$$

$$\text{Sensitivity} = \frac{\text{Number of true positives}}{\text{number of true positives} + \text{number of false negatives}}$$

Negative predictive value and positive predictive value are determined using the formula:

$$\text{negative predictive value} = \frac{\text{Number of true negatives obtained from cystoscopy}}{\text{number of true negatives obtained from cystoscopy} + \text{number of false negatives from Ammps}}$$

$$\text{positive predictive value} = \frac{\text{Number of true positives obtained from cystoscopy}}{\text{number of true positives obtained from cystoscopy} + \text{number of false positives from Ammps}}$$

Ammps provided 100% sensitivity and 95% specificity in detecting cancer when the data was compared to cystoscopy. The sensitivity and specificity of Ammps is comparable to BTA-STAT, Y and Z. Therefore, Ammps can have an impact on generating an assay that can be performed in-clinic. In order for Ammps to be applied in resource-poor settings, they should be able to follow the ASSURED guidelines recommended by WHO. Therefore, we performed cost-analysis for performing Ammps on a single patient. It was determined that the cost to perform each assay was 4.5 cents, which is affordable in several resource poor settings. On the other hand, cystoscopy costs $350-$3000 and BTA-STAT (a urine biomarker assay) costs $158 to $228. Moreover, the sensitivity and specificity determined for Ammps was comparable with several of the conventional screening tests. Ammps can also be combined with these screening tests to improve the sensitivity and specificity of the bladder cancer tests. Ammps are also user-friendly because they utilize urine samples, which are obtained via non-invasive procedures, and are comparable to BTA-STAT among others. In addition, Ammps could identify bladder cancer rapidly in less than 30 min, which is another criteria recommended by WHO, and other biomarker tests take more than 30 min to perform. For example, cystoscopy requires 1-2 h, urine cytology requires 2-3 days, and BTA-STAT requires 50 min. Ammps are performed in an instrument-free manner, which also brings down the total cost required to perform the test. Lastly, the reagents of Ammps can be stored in dry form at room temperature, and thus follow the delivered criteria of ASSURED.

In view of the many possible embodiments to which the principles of the disclosed, invention may be applied, it should be recognized that the illustrated embodiments are only preferred examples and should not be taken as limiting the scope of the invention.

What is claimed is:

1. A kit comprising:
    a composition comprising a gelatin-crosslinked aggregate of particles comprising a Fe(II)- and $Ca^{+2}$-chelated alginate; and
    a composition comprising a Fenton reagent and at least one chromogenic substrate.

2. The kit of claim 1, wherein the composition comprising a Fenton reagent and at least one chromogenic substrate comprises $H_2O_2$, HCl, at least one first chromogenic substrate, and at least one second chromogenic substrate.

3. The kit of claim 1, wherein the at least one chromogenic substrate is selected from 2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, inner salt sodium salt, or a compound having a structure of:

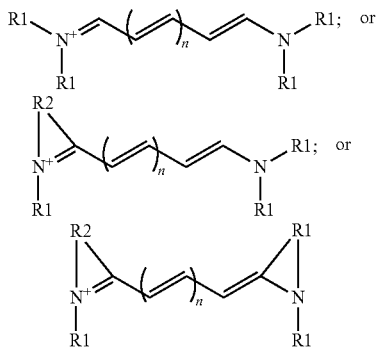

wherein n=1 to 7; and each R1 is independently an alkyl, substituted alkyl, aryl, or substituted aryl; and each R2 forms part of a ring, or
ICG, or
IR780, or
cyanine 2, or
cyanine 2.5, or
cyanine 5, or
cyanine 7.

4. The kit of claim 1, wherein the gelatin is a gelatinase-specific gelatin-type substrate.

5. The kit of claim 1, wherein the gelatin is gelatin A, gelatin B, or mixed gelatin.

6. The kit of claim 1, wherein the particles have an average particle size of at least 100 nm.

7. The kit of claim 1, wherein the particles have an average particle size of not greater than 1000 nm.

8. A method for detecting the presence of cancer in a subject, comprising:
    contacting a biological sample from the subject with a first composition comprising a gelatin-crosslinked aggregate of particles comprising a Fe(II)- and $Ca^{+2}$-chelated alginate to form a second composition; and
    contacting the second composition with a third composition that comprises a Fenton reagent and at least one chromogenic substrate resulting in an assay composition;
    wherein detection of a color change in the assay composition indicates the presence of a matrix metalloproteinase in the biological sample.

9. The method of claim 8, wherein the composition comprising a Fenton reagent and at least one chromogenic substrate comprises $H_2O_2$, HCl, at least one first chromogenic substrate, and at least one second chromogenic substrate.

10. The method of claim 8, wherein the matrix metalloproteinase is matrix metalloproteinase 2, matrix metalloproteinase 9, or both matrix metalloproteinase and matrix metalloproteinase 9.

11. The method of claim 8, wherein the cancer is prostate cancer or bladder cancer.

12. The method of claim 8, wherein the cancer can be distinguished from benign prostate hyperplasia, or wherein the cancer can be distinguished from benign conditions causing hematuria, or wherein the cancer can be distinguished from benign conditions causing both hematuria and prostate hyperplasia.

13. The method of claim 8, wherein the gelatin is a gelatinase-specific gelatin-type substrate.

14. The method of claim 8, wherein the gelatin is gelatin A, gelatin B, or mixed gelatin.

15. The method of claim 14, wherein the particles have an average particle size of 100 nm to 1000 nm.

16. The method of claim 14, wherein the cancer is prostate cancer or bladder cancer.

17. The method of claim 8, wherein the particles have an average particle size of at least 100 nm.

18. The method of claim 17, wherein the particles have an average particle size of not greater than 1000 nm.

19. The method of claim 8, wherein the at least one chromogenic substrate changes color from purple to yellow.

20. The method of claim 8, wherein the at least one chromogenic substrate is selected from 2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, inner salt sodium salt, or a compound having a structure of:

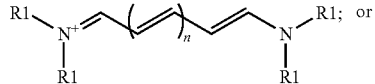

-continued

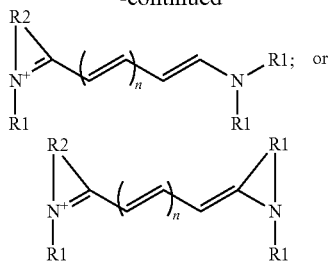

wherein n=1 to 7; and each R1 is independently an alkyl, substituted alkyl, aryl, or substituted aryl; and each R2 forms part of a ring, or ICG, or
IR780, or
cyanine 2, or
cyanine 2.5, or
cyanine 5, or
cyanine 7.

21. The method of claim 8, wherein the composition comprising a Fenton reagent and at least one chromogenic substrate includes only a single chromogenic substrate.

22. The method of claim 21, wherein the single chromogenic substrate is selected from 2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, inner salt sodium salt, or a compound having a structure of:

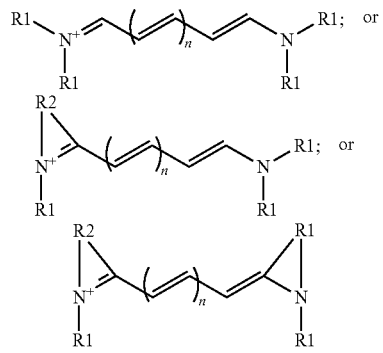

wherein n=1 to 7; and each R1 is independently an alkyl, substituted alkyl, aryl, or substituted aryl; and each R2 forms part of a ring, or ICG, or
IR780, or
cyanine 2, or
cyanine 2.5, or
cyanine 5, or
cyanine 7.

23. The method of claim 8, wherein the biological sample is human urine.

24. A method for detecting the presence of cancer in a subject, comprising:
contacting a biological sample from the subject with a first composition comprising a gelatin-crosslinked aggregate of particles comprising a Fe(II)- and $Ca^{+2}$-chelated alginate to form a second composition; and
contacting the second composition with an acid, $H_2O_2$, and at least one chromogenic substrate resulting in an assay composition;
wherein detection of a color change in the assay composition indicates the presence of a matrix metalloproteinase in the biological sample.

25. The method of claim 24, wherein the biological sample is human urine.

26. The method of claim 24, wherein the cancer is prostate cancer or bladder cancer.

27. The method of claim 24, wherein the at least one chromogenic substrate changes color from purple to yellow.

28. The method of claim 24, wherein the acid is selected from HBr, $H_2S$, HCl, or a mixture thereof.

29. A method comprising:
contacting a biological sample from a subject with a gelatin-crosslinked aggregate of particles comprising a Fe(II)- and $Ca^{+2}$-chelated alginate;
generating individual particles via gelatinase-mediated cleavage of the gelatin crosslinks between the particles, wherein the gelatinase is present in the biological sample; and
contacting the individual particles with an acid, $H_2O_2$, and at least one chromogenic substrate.

30. The method of claim 29, wherein the gelatinase is matrix metalloproteinase 2, matrix metalloproteinase 9, or both matrix metalloproteinase and matrix metalloproteinase 9.

31. The method of claim 29, wherein the biological sample is human urine.

32. The method of claim 29, wherein the particles have an average particle size of 100 nm to 1000 nm.

33. The method of claim 29, wherein the acid is selected from HBr, $H_2S$, HCl, or a mixture thereof.

* * * * *